(12) United States Patent
Lin et al.

(10) Patent No.: US 7,820,372 B2
(45) Date of Patent: Oct. 26, 2010

(54) DUAL-BAND MICRO-PLANAR INVERTED F ANTENNA USED FOR BIOMOLECULAR FINGER PRINT AND ITS IDENTIFICATION METHOD

(75) Inventors: Chii-Wann Lin, Taipei (TW); Nan-Fu Chiu, Taipei (TW); Chih-Kung Lee, Taipei (TW); Kuang-Chong Wu, Taipei (TW)

(73) Assignee: National Taiwan University, Taipei (TW)

( * ) Notice: Subject to any disclaimer, the term of this patent is extended or adjusted under 35 U.S.C. 154(b) by 402 days.

(21) Appl. No.: 12/026,441

(22) Filed: Feb. 5, 2008

(65) Prior Publication Data

US 2009/0107216 A1 Apr. 30, 2009

(30) Foreign Application Priority Data

Oct. 30, 2007 (TW) .............................. 96140873 A

(51) Int. Cl.
*C12Q 1/00* (2006.01)
(52) U.S. Cl. .......................... 435/4; 73/53.01; 73/54.17
(58) Field of Classification Search ...................... None
See application file for complete search history.

(56) References Cited

U.S. PATENT DOCUMENTS 4,679,426 A * 7/1987 Fuller et al. ................ 73/53.01

\* cited by examiner

*Primary Examiner*—NC Yang
(74) *Attorney, Agent, or Firm*—WPAT, P.C.; Anthony King

(57) ABSTRACT

The present invention relates to a dual-band micro-planar inverted F antenna (MPIFA), which is made based on a new type of printed circuit board (PCB), and its identification method to all different biomolecular concentration. This device works under 3 GHz and 7 GHz microwave frequency bands, and can predict the relationship for different absorbed biomolecular concentrations versus frequencies with the impedance value, dB(S(1,1)) parameter, and the variance of phase versus the frequency obtained from the measurement.

8 Claims, 10 Drawing Sheets

Top view

Obliqe view

Top view

Obliqe view

Table 1. Refractive index (n), resonate frequency shift and resonate impedance on 3GHz variation.

| material | n | drift freq. | impedance |
|---|---|---|---|
| D.I. Water | 1.3319 | 1.4GHz | 40.57773983 |
| NaCl 10mM | 1.3322 | 1.8 GHz | 42.1965938 |
| NaCl 50mM | 1.3324 | 1.8 GHz | 47.19938739 |
| NaCl 0.1M | 1.333 | 1.8 GHz | 51.66908434 |
| Glu 0.0625M | 1.3336 | 1.9 GHz | 53.43702755 |
| Glu 0.125M | 1.3353 | 1.9 GHz | 66.13204413 |
| Glu 0.25M | 1.3386 | 1.9 GHz | 70.2629762 |
| alcohol 50% | 1.3563 | 2 GHz | 76.10216502 |
| alcohol 70% | 1.3583 | 2 GHz | 106.5512021 |
| alcohol 100% | 1.3585 | 2 GHz | 111.1772209 |

Table 2. Refractive index (n), resonate frequency shift and resonate impedance on 7 GHz variation.

| material | n | drift freq. | impedance |
|---|---|---|---|
| D.I. Water | 1.3319 | 4.6 GHz | 51.45207 |
| NaCl 10mM | 1.3322 | 4.1 GHz | 38.55197 |
| NaCl 50mM | 1.3324 | 4.1 GHz | 42.74873 |
| NaCl 0.1M | 1.333 | 4.1 GHz | 46.94888 |
| Glu 0.0625M | 1.3336 | 4.1 GHz | 44.87288 |
| Glu 0.125M | 1.3353 | 4.1 GHz | 46.86993 |
| Glu 0.25M | 1.3386 | 4.3 GHz | 54.97497 |
| alcohol 50% | 1.3563 | 4.1 GHz | 50.06923 |
| alcohol 70% | 1.3583 | 4.2 GHz | 32.24915 |
| alcohol 100% | 1.3585 | 4.2 GHz | 29.24143 |

DUAL-BAND MICRO-PLANAR INVERTED F ANTENNA USED FOR BIOMOLECULAR FINGER PRINT AND ITS IDENTIFICATION METHOD

TECHNICAL FIELD

The present invention relates to a device and a method for biomolecular identification using microwave frequency, and particularly to a method and a device for applying dual-band antenna on biomolecular identification technology.

BACKGROUND OF THE INVENTION

Recently, due to the continuous development of semiconductor processing technology, the biomedical micro-sensing technology also has significant growth on its development. In the domain of bio-sensing technology, it could be approximately divided into two types of inspection methods, i.e. inspection on chemical reaction amount and physical reaction amount. However, it could be classified into electrochemical theory and electromagnetic theory based on the inspection theory, in which the electromagnetic theory includes the optical inspection, electrical inspection, sound wave inspection and microwave inspection methods.

The Surface Plasmon Resonance (SPR) method and the Raman Spectrum measurement method are the current dominant sensing technologies. However, for the inspection system of these inspection methods, the important components, such as laser source, optical loop system, and optical components, are difficult to be miniaturized, so that the entire inspection system could not be developed toward a complete micro system. Moreover, for the technology of sound wave inspection and microwave inspection, it employs the Surface Acoustic Wave (SAW) transducer and quartz crystal microbalance (QCM) transducer as the major inspection components, in which both of the SAW transducer and the QCM transducer employ the piezoelectric quartz crystal as the material. The SAW transducer is excited by applying voltage on the metal film inter digital transducer (IDT) on the surface having piezoelectric material, so, when the boundary conditions on the wave conduction path have been changed, the characteristics of sound wave, such as wave speed, phase or amplitude, will also be changed accordingly. The QCM transducer uses the quartz crystal itself as the material, which employs the frequency generated by the oscillation of quartz crystal itself to detect the variation on the concentration of the inspected subject, and the outcome comes from the characteristic of inversed piezoelectric effect of the quartz itself. When applying electric field on the surface of the quartz crystal, the quartz crystal will be oscillated to achieve the purpose of detecting the concentration variation.

The SAW and QCM transducer themselves both have multiple advantages, such as simplified theory, easy operation, low cost, repetitive use of chips, light instrument, and real-time response. However, due to a certain limitation on the working frequency, the typical working frequency of the SAW transducer is only at hundreds of MHz, and the typical working frequency of the QCM transducer is only at tens of MHz. Because of the influence by the limitation from the intrinsic physical characteristics, both inspection methods are subjected to great limitations on the sensitivity, resolution and Signal-to-Noise ratio (SNR).

SUMMARY OF INVENTION

In order to solve the problems in the prior art, the present invention discloses a new inspection method and device of PCB-based dual-band micro-planar inverted F antenna (Dual-band MPIFA) for the correlated measurement on the reaction variation between the absorbed masses by the biomolecules versus different concentrations. The inspection method using the dual-band MPIFA according to the present invention could provide with the advantages from the conventional SAW transducer measurement method and the QCM transducer measurement method, such as easy operation, low cost, repetitive usage, light instrument and real-time response, and further provide the functions of dual frequency calibration, i.e. 3 GHz and 7 GHz, and concurrent analysis on multiple parameters, which are preferred than the prior art. It could be appreciated from the following experiment results that the variance generated by the frequency could be applied for very sensitive inspection on the variation of bio-molecule absorbed mass. The system according to the present invention could further be developed toward the application development of systemized of sensing components, and integrate the planar processing technology of dual-band MPIFA with the integrated circuit to form the Monolithic Microwave Integrated Circuits (MMIC). This kind of integration could enable the sensing technology further meeting the requirement of microminiaturization and high efficiency.

DETAILED DESCRIPTION OF PREFERRED EMBODIMENTS

Figure 1:
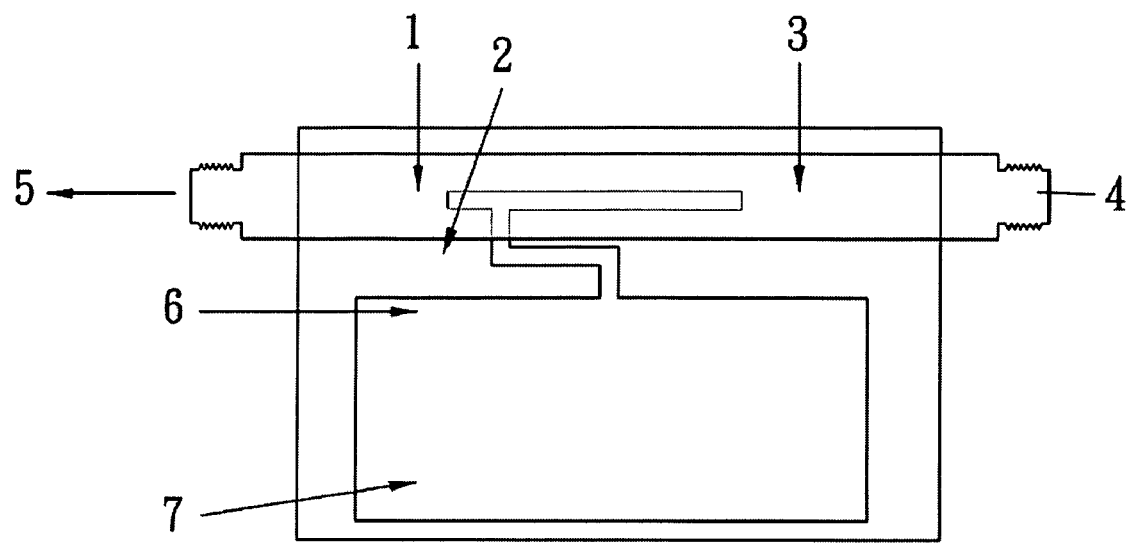
FIG. 1 is a plane view and oblique drawing for the dual-band MPIFA.
Figure 1:
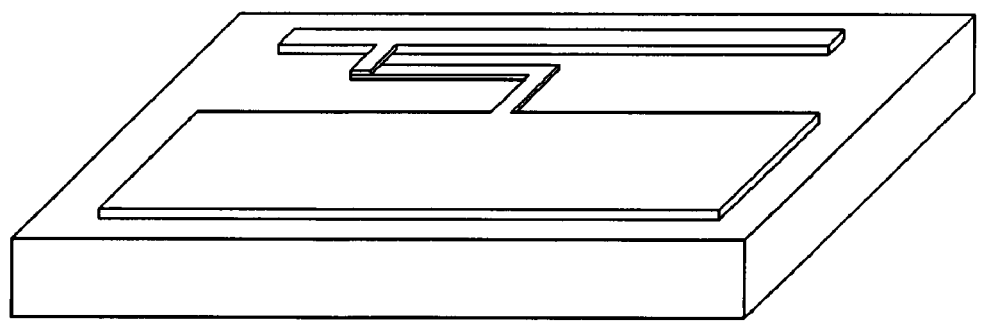

In order for the examination members to understand the objects, features and effects of the present invention, the present invention will be described in details with the following embodiments associated with the attached figures.

The antenna sensing theory is based on the measurement of central frequency drift caused by the loss of dielectric constant ($\epsilon_r$) for the inspected subject on the antenna medium. When the loss of medium becomes larger, the central frequency drift will also be larger, so the sensitivity will be better and following with increased quality factor, reduced bandwidth and lower gain. The technique in the present invention employs the amount of bio-molecule mass absorbed on the antenna surface to influence the oscillation frequency of the antenna itself, and further cause the change of oscillation frequency; the frequency variation is in proportion to the bio-molecule mass absorbed by the antenna itself. The more the absorbed mass is, the larger the reduction of frequency will be.

In the present invention, the antenna for the measurement is not specifically limited on the types, which could be microstrip antenna, inversed F antenna, YAGI antenna, shortwave antenna, super shortwave antenna, microwave antenna, directional antenna, non-directional antenna, wideband antenna, modulation antenna, vertical antenna, inversed L antenna, T antenna, umbrella antenna, whip antenna, symmetrical antenna, cage antenna, angle antenna, folded antenna, V antenna, diamond antenna, discone antenna, fishbone antenna, harp antenna, dual-awl antenna, parabolic antenna, horn parabolic antenna, horn antenna, horn lens antenna, lens antenna, opened tank antenna, medium antenna, periscope antenna, spiral antenna or other three-dimensional and planar antennas for sending sensing signals in micro frequency band, 50 MHz~40 GHz, for measurement of parameter variation.

In the present invention, the object parameters measured by the antenna includes the variation of impedance with the variation range of 0~100 Ohm, the variation range of frequency between 50 MHz and 40 GHz, the amount of $S(1,1)$ parameter between 100 and −100, and the variation of different phases, in which all the measurement chart values, as shown in FIG. 2 to FIG. 8, could be obtained through the variation of Smith Chart.

In the present invention, the subjects to be measured are not limited to organic solvents, and may be an aqueous solution containing bio-molecule(s) selected from proteins, amino acids, saccharides, lipids, vitamins, minerals, oligoenzymes, nucleotides, oligonucleotides, nucleic acid etc.; or an aqueous solution containing ionic compound(s) selected from sodium salts, potassium salts, lithium salts, phosphate salts, borate salts, bromide salts, fluoride salts, carbonates, calcium chloride, magnesium chloride, sodium citrate, sodium acetate, calcium lactate, magnesium sulfate, sodium fluoride etc.

Measurement Method According to the Present Invention

The measurement method for the PCB-based dual-band MPIFA according to the present invention is as follows:

The Agilent 8722ES (50 MHz~40 GHz) vector network analyzer is used for the measurement with the measurement range configured between 100 MHz to 40 GHz. The measurement method is to immerse the antenna, such as the dual-band MPIFA shown in FIG. 1, into the detected solution as the configuration shown in FIG. 4 in the environment with ambient temperature of 26° C. and relative humidity of 65%. The main oscillator of the antenna has the length of ¼λ. At the linear F head of MPIFA, it should be grounded at ⅕ from the top of the F head, and provided with a planar hole beside the body of MPIFA.

Figure 2:
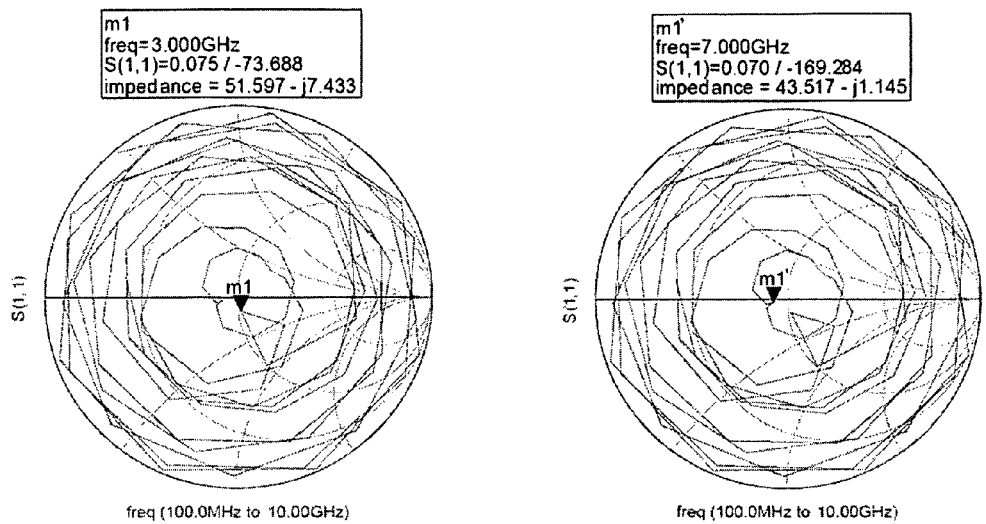
FIG. 2 is a measurement result with Smith chart in the air for the dual-band MPIFA.
Figure 3:
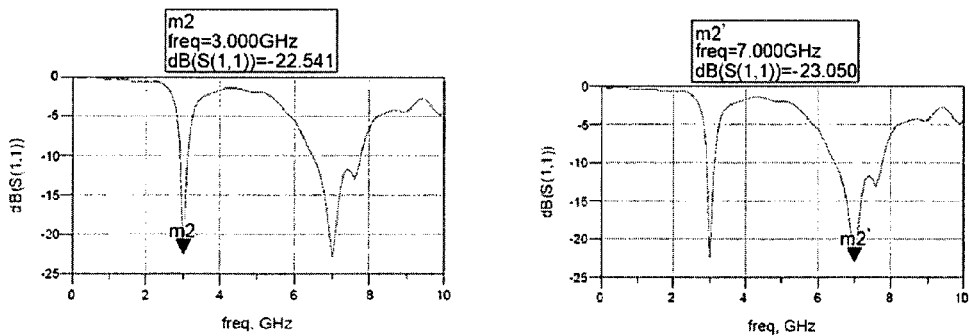
FIG. 3 is a measurement result of a typical Db(S(1,1)) in the air for the dual-band MPIFA.
Figure 4:
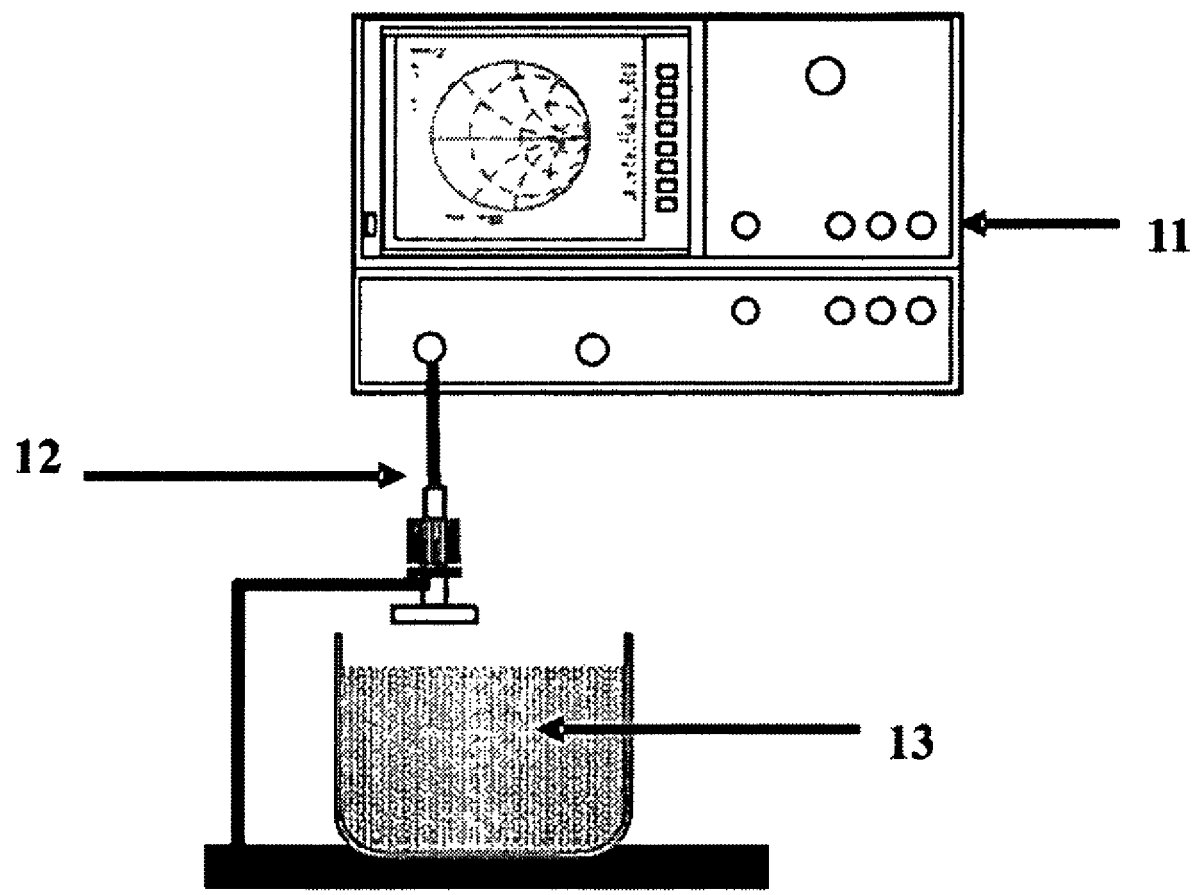
FIG. 4 is a dual-band MPIFA sensing solution measurement system.

As shown in FIG. 1, the sensing chip is measuring with the sensing microwave frequency band at dual frequencies of 3 GHz and 7 GHz, and obtains the Smith chart measurement result as shown in FIG. 2, and the measurement result of a typical S parameter $S(1,1)$ as shown in FIG. 3, wherein the $S(1,1)$ in S parameter is an input match-impedance.

In FIG. 2, m1 indicates the measurement under 3 GHz, m1' indicates the measurement under 7 GHz, and $S(1,1)$ indicates the refractive index including the front real portion and the rear imaginary portion, and the impedance also includes the real portion and the imaginary portion. As shown in FIG. 2, the obtained impedance measurement in the air for m1 portion is 51.59 Ohm, and the obtained impedance measurement in the air for m1' portion is 43.51 Ohm, and the value is close to the factory default value 50 Ohm of an ordinary standard antenna. In the Smith chart, each turning point on the curve indicates the impedance under different frequencies, as shown in FIG. 2, at the frequencies of 3 GHz and 7 GHz, it could obtain the impedance closer to 50 Ohm than under the measurement frequencies within other range, so the default receiving and emitting frequencies of the antenna according to the present invention is 3 GHz and 7 GHz. FIG. 3 is a diagram for the measured $dB(S(1,1))$ in the air under 3 GHz (m1) frequency and 7 GHz (m1') frequency, in which the meaning of $dB(S(1,1))$ is the level of amount change of $S(1,1)$ parameter. Thus, the Smith chart in FIG. 3 could be combined with FIG. 2 to deduce the meaning for the impedance and the amount variation for $S(1,1)$ parameter. With the measurement as the contents in FIG. 2 and FIG. 3, it could known that the determined measurement features for the antenna by default calibration at the factory is compared with the measurement of impedance drift, frequency drift and amount variation of $S(1,1)$ parameter of the dual-band MPIFA in each embodiment based on the above-mentioned method, and then it could be used as a bio-sensor. The inspection method is to distinguish the concentration and molecule composition of different liquid measured subject through the variation of frequency and impedance by touching the liquid measured substance. When the concentration or molecular characteristics has changed, the values for impedance, frequency, and amount of $S(1,1)$ parameter will be drifted, so, by comparing the drift volume resulted therefrom with the figure finger print in the Smith chart, the inspected subject could be obtained with the concentration and the possible molecular types.

EXAMPLE ONE

The Agilent 8722ES (50 MHz~40 GHz) vector network analyzer is used for the measurement with the measurement range configured between 100 MHz to 40 GHz and the ambient temperature at 26° C. and the relative humidity at 65%. With the above-mentioned measurement on the blank parameter values in the air for the antenna according to the present invention, it is to immerse the antenna into a deionized water, and measure the variation of drift on the impedance, frequency and amount of $S(1,1)$ parameter caused by the deionized water, and obtain the figure finger print corresponding to the Smith chart based on the concentration and molecule structure of the inspected subject.

Figure 5:
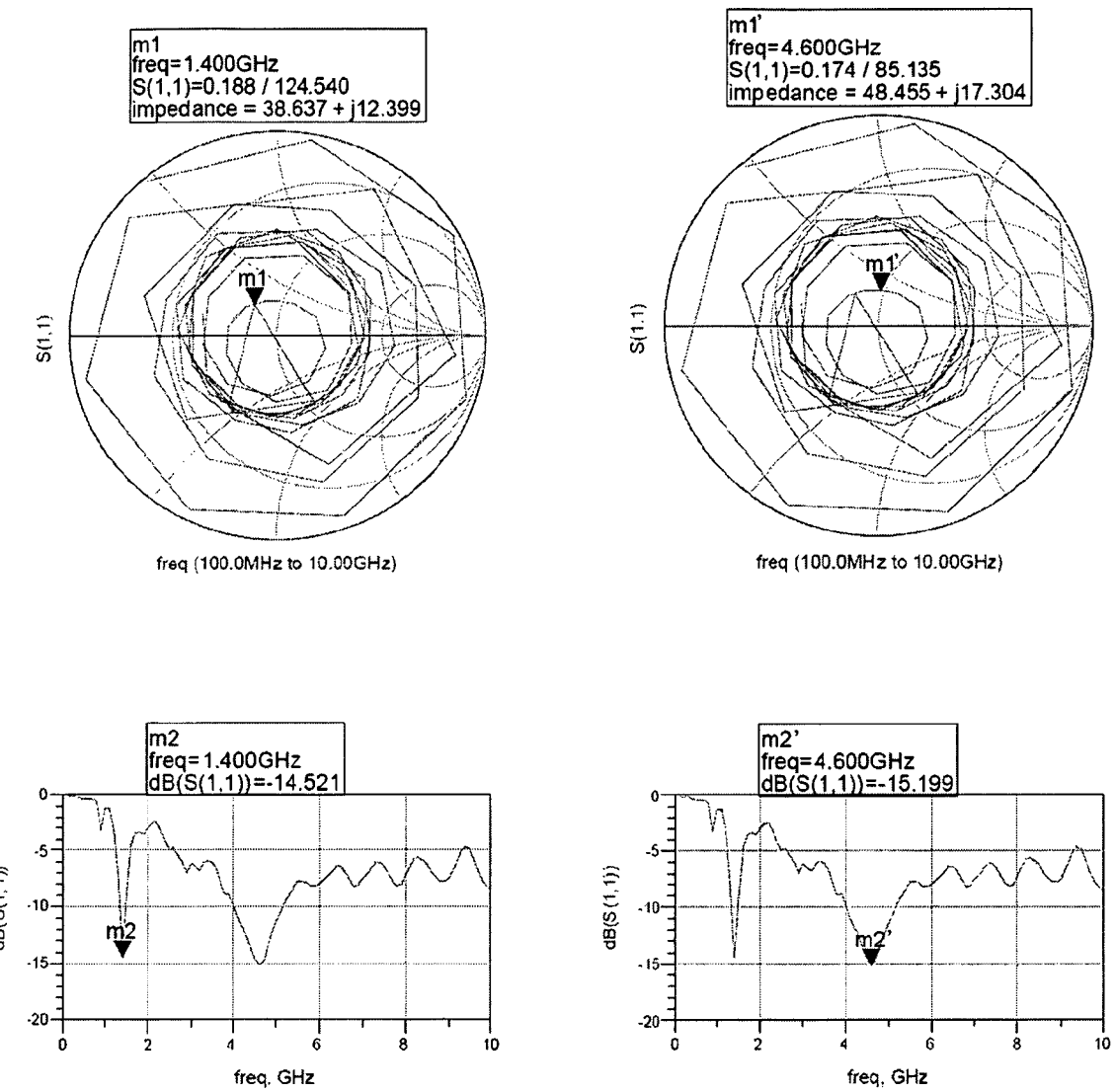
FIG. 5 is the Smith chart, frequency, and displacement of dB measured for the dual-band MPIFA in a deionized solution.

The measurement result is shown in FIG. 5. It could be viewed from FIG. 5 that, when the frequency is at 3 GHz(m1), the impedance Z is (38.637+j12.399), the strength is 0.188, and the phase is 124.540; when the frequency is at 7 GHz (m1'), the measurement result shows that the impedance Z is (48.455+j17.304), the strength is 0.174, and the phase is 85.135. At the right of FIG. 5, the measurement result indicates the $dB(S(1,1))$ being −14.521 for $S(1,1)$ at 3 GHz(m2), and the dB(S(1,1)) being 15.199 at 7 GHz (m2'), and m2 frequency is drifted to 1.4 GHz, and m2' frequency is drifted to 4.6 GHz.

EXAMPLE TWO

The Agilent 8722ES (50 MHz~40 GHz) vector network analyzer is used for the measurement with the measurement range configured between 100 MHz to 40 GHz and the ambient temperature at 26° C. and the relative humidity at 65%. For the above-mentioned measurement on the blank parameter values in the air for the antenna according to the present invention, the method is to immerse the radio frequency (RF) transmission wire into a NaCl solution with the concentrations at 10 mM, 50 mM and 0.1M, respectively, and measure the variation of drift on the impedance, frequency and amount of S(1,1) parameter caused by the immersion, and obtain the figure finger print corresponding to the Smith chart based on the concentration and molecule structure of the inspected subject.

Figure 6:
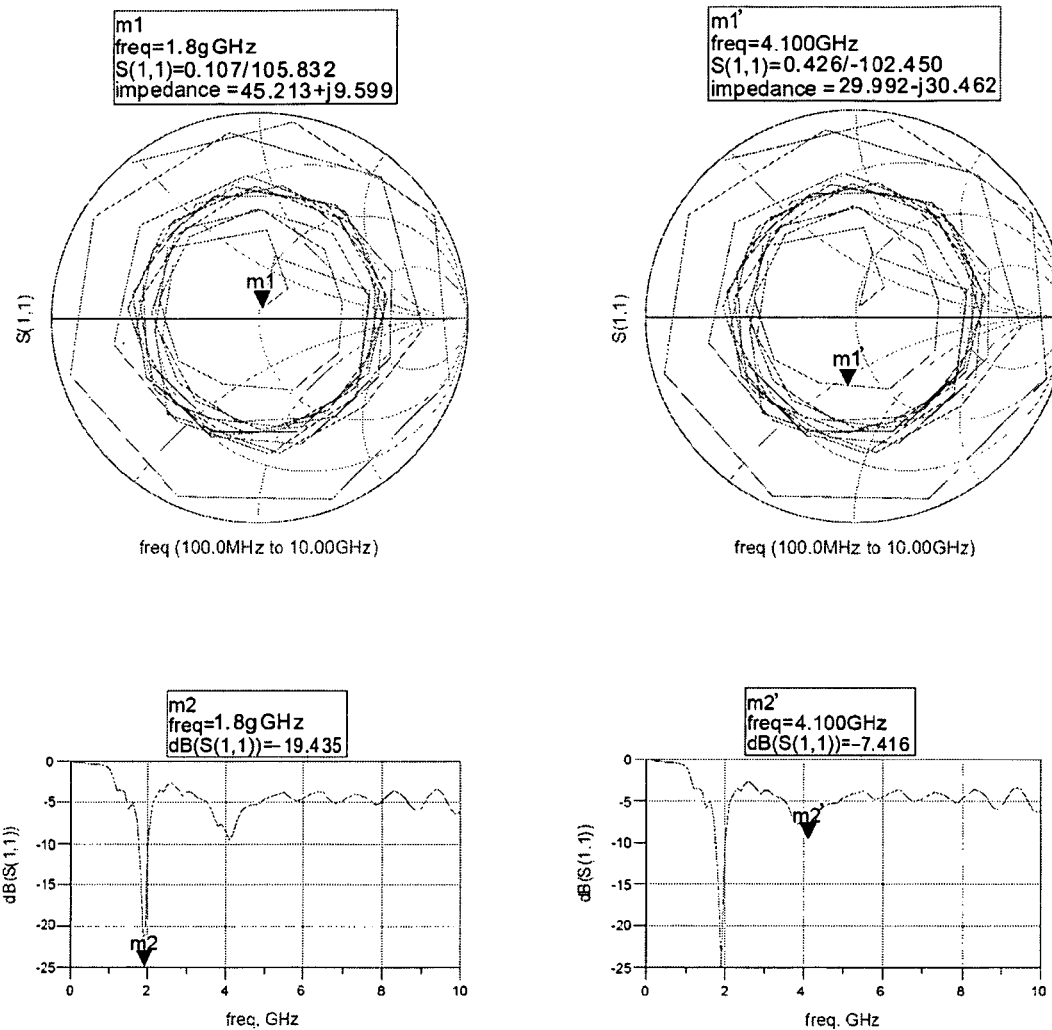
FIG. 6 is the Smith chart, frequency, and displacement of dB measured for the dual-band MPIFA in aqueous solution of 0.1 M NaCl.

The measurement result is shown in FIG. 6. It could be viewed from FIG. 6 that, when the frequency is at 3 GHz(m1), the impedance Z is (46.213+j9.599), the strength is 0.107, and the phase is 105.832; when the frequency is at 7 GHz(m1'), the measurement result shows that the impedance Z is (29.992−j30.462), the strength is 0.426, and the phase is −102.450. At the right of FIG. 6, the measurement result indicates the dB(S(1,1)) being −19.435 for S(1,1) at 3 GHz (m2), and the dB(S(1,1) being 7.416 at 7 GHz (m2'), and m2 frequency is drifted to 1.8 GHz, and m2' frequency is drifted to 4.1 GHz.

EXAMPLE THREE

The Agilent 8722ES (50 MHz~40 GHz) vector network analyzer is used for the measurement with the measurement range configured between 100 MHz to 40 GHz and the ambient temperature at 26° C. and the relative humidity at 65%. With the above-mentioned measurement on the blank parameter values in the air for the antenna according to the present invention, it is to immerse the radio frequency (RF) transmission wire into a glucose solution with the concentrations at 0.0625 M, 0.125 M, and 0.25M, respectively, and measure the variation of drift on the impedance, frequency and amount of S(1,1) parameter caused by the immersion, and obtain the figure finger print corresponding to the Smith chart based on the concentration and molecule structure of the inspected subject.

Figure 7:
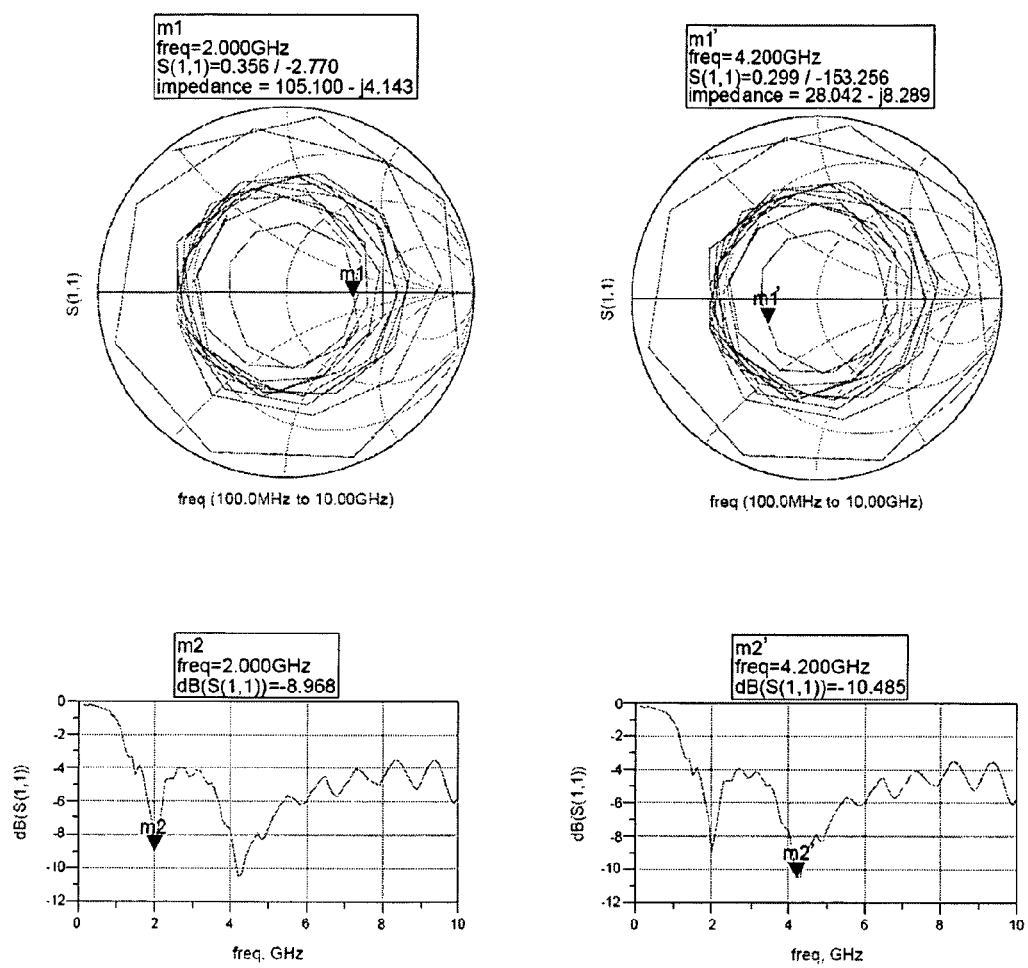
FIG. 7 is the Smith chart, frequency, and displacement of dB measured for the dual-band MPIFA in 100% aqueous solution of alcohol.

The measurement result is shown in FIG. 7. It could be viewed from FIG. 7 that, when the frequency is at 3 GHz(m1), the impedance Z is (105.1−j4.143), the strength is 0.356, and the phase is −2.770; when the frequency is at 7 GHz(m1'), the measurement result shows that the impedance Z is (28.042−j8.289), the strength is 0.299, and the phase is −153.256. At the right of FIG. 7, the measurement result indicates the dB(S(1,1)) being −8.968 for S(1,1) at 3 GHz(m2), and the dB(S(1,1) being −10.485 at 7 GHz (m2'), and m2 frequency is drifted to 2.0 GHz, and m2' frequency is drifted to 4.2 GHz.

EXAMPLE FOUR

The Agilent 8722ES (50 MHz~40 GHz) vector network analyzer is used for the measurement with the measurement range configured between 100 MHz to 40 GHz and the ambient temperature at 26° C. and the relative humidity at 65%. With the above-mentioned measurement on the blank parameter values in the air for the antenna according to the present invention, it is to immerse the radio frequency (RF) transmission wire into an alcohol solution with the concentrations at 50%, 70%, and 100%, respectively, and measure the variation of drift on the impedance, frequency and amount of S(1,1) parameter caused by the immersion, and obtain the figure finger print corresponding to the Smith chart based on the concentration and molecule structure of the inspected subject.

Figure 8:
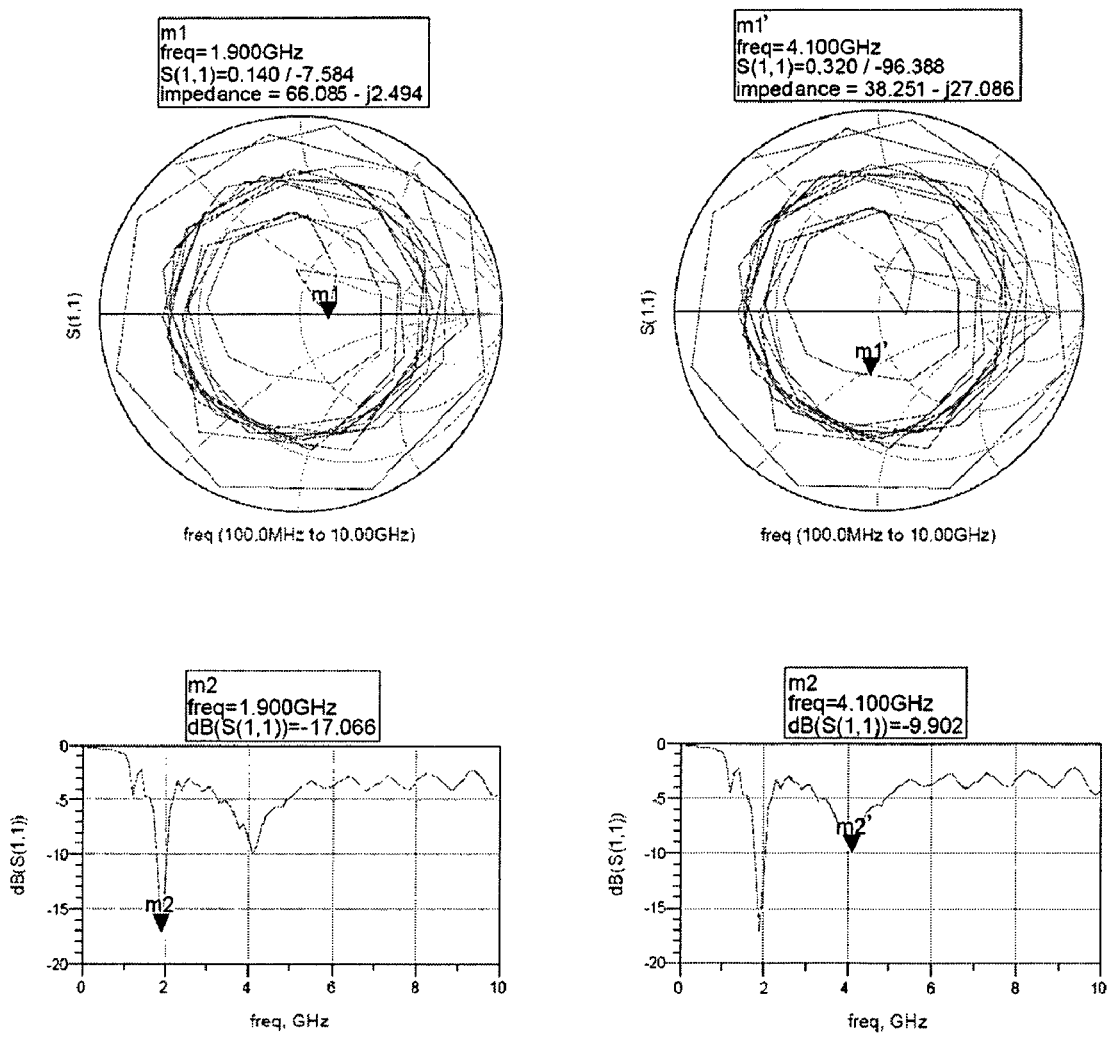
FIG. 8 is the Smith chart, frequency, and displacement of dB measured for the dual-band MPIFA in 0.125 M aqueous solution of glucose.

The measurement result is shown in FIG. 8. It could be viewed from FIG. 8 that, when the frequency is at 3 GHz(m1), the impedance Z is (66.085−j2.494), the strength is 0.140, and the phase is −7.584; when the frequency is at 7 GHz(m1'), the measurement result shows that the impedance Z is (38.251−j27.086), the strength is 0.320, and the phase is −96.388. At the right of FIG. 8, the measurement result indicates the dB(S(1,1)) being −17.066 for S(1,1) at 3 GHz(m2), and the dB(S(1,1) being −9.902 at 7 GHz (m2'), and m2 frequency is drifted to 1.9 GHz, and m2' frequency is drifted to 4.1 GHz.

Experiment Result

Figure 9:
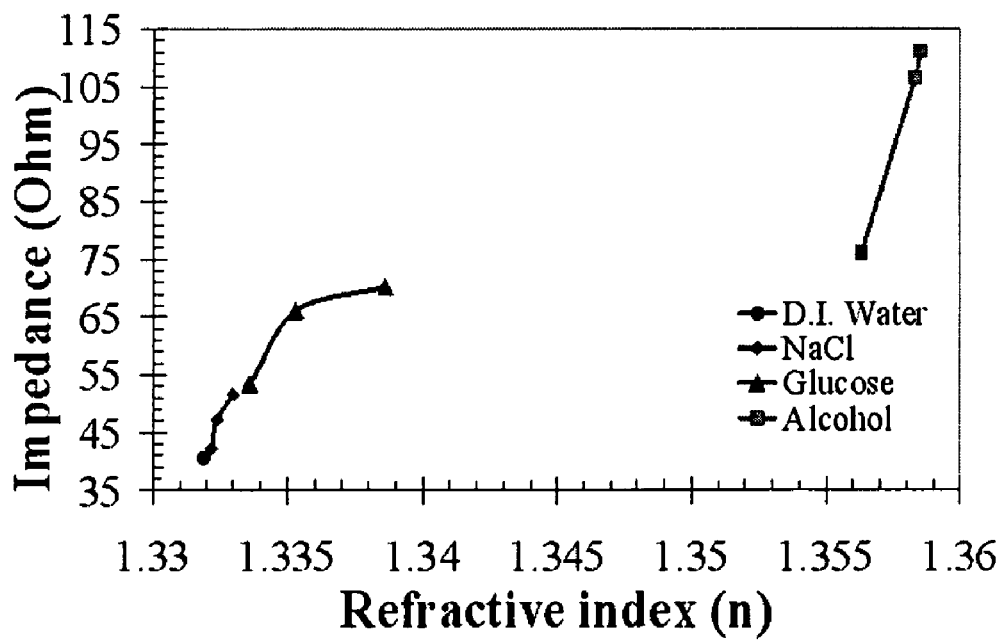
FIG. 9 is a variation relationship of different solution and different concentration versus the total impedance with coordinates for the drift measurement result with the working frequency at 3 GHz.

It could be found by analyzing the experiment result that, as shown in FIG. 9, the measurement for drifting generated under 3 GHz indicates in the figure that the increasing of refractivity and the impedance is exhibited with an incremental relationship, and providing the same central oscillation frequency in all the same solution.

Figure 10:
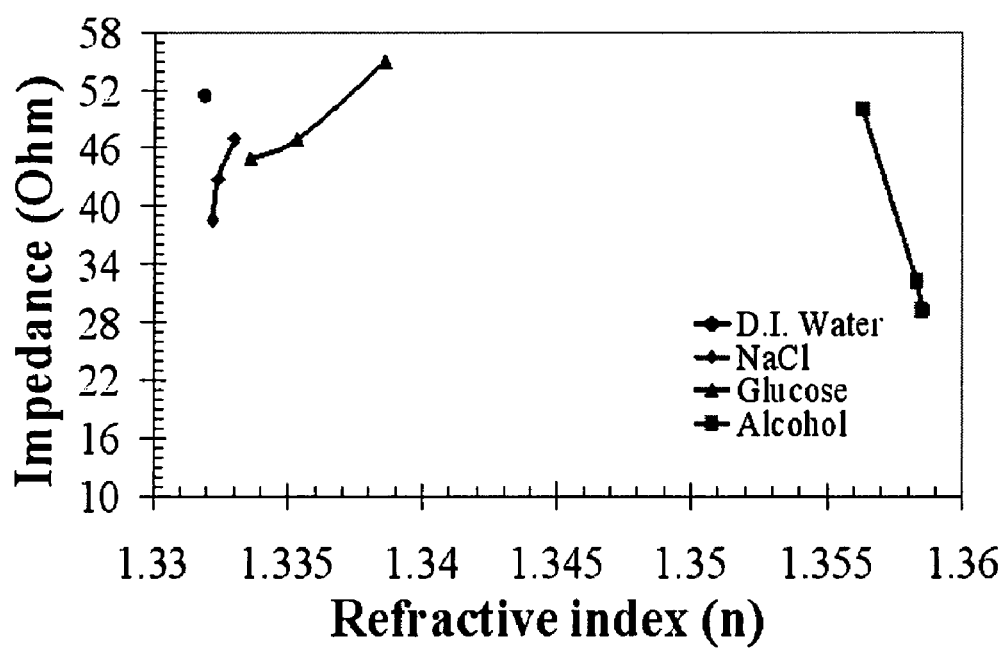
FIG. 10 is the drift measurement with the working frequency at 7 GHz.
Figure 11:
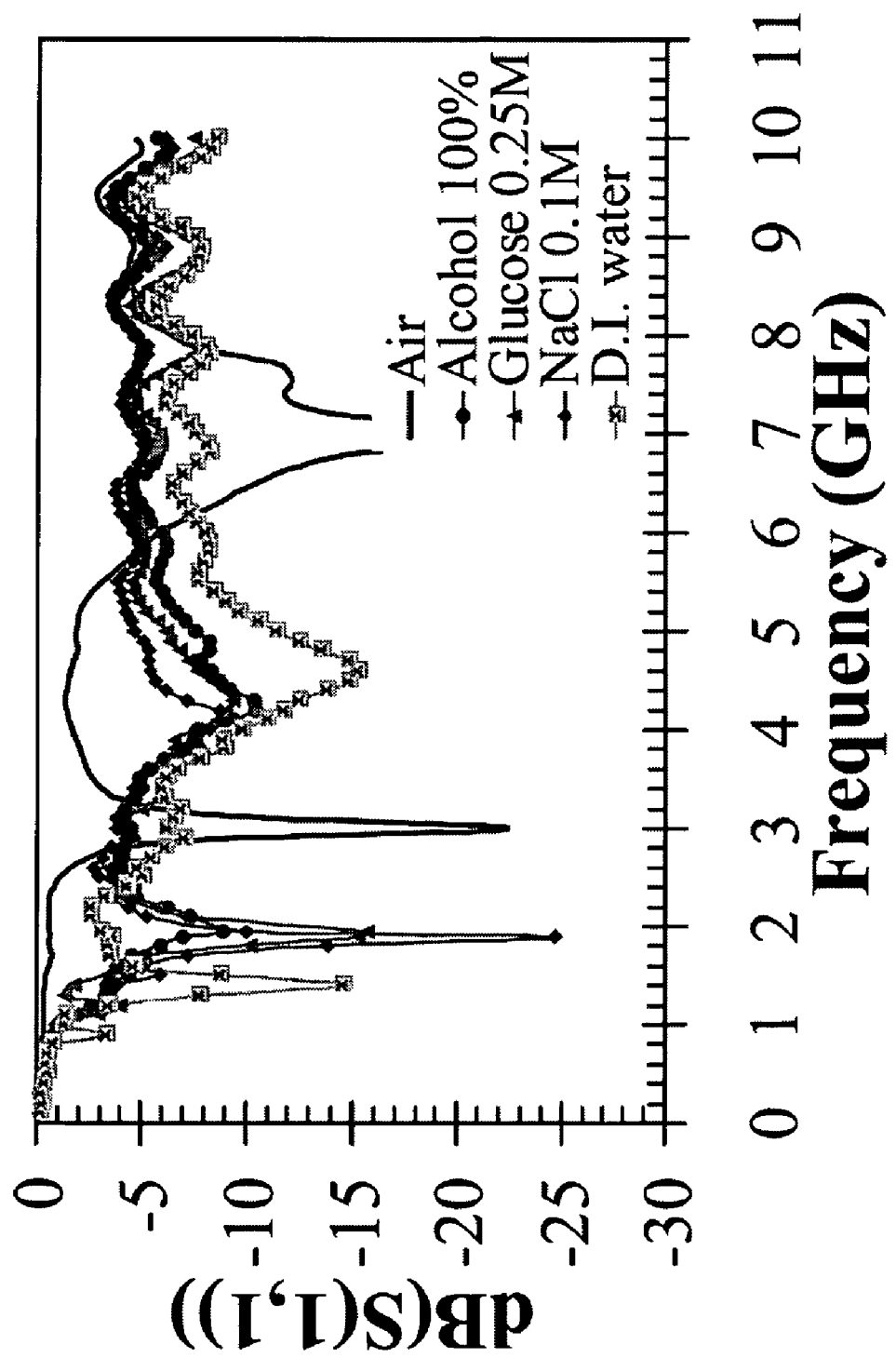
FIG. 11 shows the dB(S(1,1) versus frequency in each measurement sample solution.

Furthermore, FIG. 10 shows a drift measurement diagram with frequency at 7 GHz. It could be known from the figure that, when the refractivity is increasing, the impedance to NaCl and glucose is exhibited with an incremental relationship, but with a decremental relationship for the impedance to alcohol. In a summary of the analysis result, we could discover that the drift variation in high frequency band could more precisely identify the spectrums of different molecular solutions in association with the variation in low frequency band.

What is claimed is:

1. A method for identifying and measuring the concentration of bio or chemical molecules in a solution, comprising the following steps:
    (1) placing a dual-band antenna in a blank solution, generating a sensing microwave frequency band at dual working frequencies between 1 GHz and 40 GHz, and measuring the parameters for the antenna, comprising frequency, amount of S(1,1) parameter, impedance, and phase variation;
    (2) placing the antenna in a measured solution comprising bio or chemical molecules to be identified or measured, generating a second sensing microwave frequency band at the same frequencies as the previous step for parameter measurement, allowing the frequency, impedance, S(1,1) parameter, and phase variation to drift due to the presence of the bio or chemical molecules in the solution, and measuring the change in frequency, S(1,1) parameter, impedance, and phase variation; and
    (3) determining the molecular type and concentration of the bio or chemical molecules in the measured solution using a table or chart correlating changes in parameters with molecular characteristics and concentration.

2. A method according to claim 1, wherein the dual-band working Frequences are at 1 to 5 GHz, and 6 to 10 GHz.

3. A method according to claim 1, wherein the dual-band antenna is made with a planar printed circuit board.

4. A method according to claim 1, wherein the antenna is capable of measuring a range of frequency between 50 MHz and 40 GHz.

5. A method according to claim 1, wherein the antenna is capable of measuring a variation in impedance between 0 and 100 Ohm.

6. A method according to claim 1, wherein the antenna is capable of measuring a drifted value of amount of S(1,1) parameter that is between 100 and −100.

7. A method according to claim 2, wherein the antenna comprises one of a microstrip antenna, inversed F antenna, YAGI antenna, shortwave antenna, super shortwave antenna, microwave antenna, directional antenna, non-directional antenna, wideband antenna, modulation antenna, vertical antenna, inversed L antenna, T antenna, umbrella antenna, whip antenna, symmetrical antenna, cage antenna, angle antenna, folded antenna, V antenna, diamond antenna, discone antenna, fishbone antenna, harp antenna, dual-awl antenna, parabolic antenna, horn parabolic antenna, horn antenna, horn lens antenna, lens antenna, opened tank antenna, medium antenna, periscope antenna, spiral antenna or other three- dimensional and planar antennas for sending sensing signals in micro frequency band (50 MHz-40 GHz) for measurement of parameter variation.

8. A method according to claim 2, wherein the antenna is placed in an aqueous solution containing bio-molecule(s) selected from proteins, amino acids, saccharides, lipids, vitamins, minerals, oligoenzymes, nucleotides, oligonucleotides, nucleic acid etc.; or an aqueous solution containing ionic compound(s) selected from sodium salts, potassium salts, lithium salts, phosphate salts, borate salts, bromide salts, fluoride salts, carbonates, calcium chloride, magnesium chloride, sodium citrate, sodium acetate, calcium lactate, magnesium sulfate, sodium fluoride.

* * * * *